(12) United States Patent
Li et al.

(10) Patent No.: US 7,074,394 B2
(45) Date of Patent: Jul. 11, 2006

(54) STABLE ALUMINUM/ZIRCONIUM ANTIPERSPIRANT SOLUTION FREE OF AMINO ACID AND POLYHYDRIC ALCOHOL

(75) Inventors: Zijun Li, Westfield, NJ (US); Jawahar Parekh, Livingston, NJ (US)

(73) Assignee: Reheis, Inc., Berkeley Heights, NJ (US)

( * ) Notice: Subject to any disclaimer, the term of this patent is extended or adjusted under 35 U.S.C. 154(b) by 505 days.

(21) Appl. No.: 10/625,038

(22) Filed: Jul. 22, 2003

(65) Prior Publication Data

US 2005/0019287 A1  Jan. 27, 2005

(51) Int. Cl.
*A61Q 15/00* (2006.01)
*A61K 8/00* (2006.01)
*A61K 8/02* (2006.01)

(52) U.S. Cl. .......................... 424/65; 424/66; 424/68; 424/400; 424/401

(58) Field of Classification Search .................. 424/65, 424/66, 68
See application file for complete search history.

(56) References Cited

U.S. PATENT DOCUMENTS

| | | | |
|---|---|---|---|
| 2,814,584 A | 11/1957 | Daley | |
| 2,814,585 A | 11/1957 | Daley | |
| 2,854,382 A | 9/1958 | Grad | |
| 2,906,668 A | 9/1959 | Beckman | |
| 3,009,769 A | 11/1961 | Grote | |
| 3,009,860 A | 11/1961 | Grote | |
| 3,405,153 A | 10/1968 | Jones et al. | |
| 3,903,258 A | 9/1975 | Siegal | |
| 4,775,528 A | 10/1988 | Callaghan et al. | |
| 5,114,705 A | 5/1992 | Callaghan et al. | |
| 5,225,187 A | 7/1993 | Carmody | |
| 5,486,347 A | 1/1996 | Callaghan et al. | |
| 5,589,196 A | 12/1996 | Callaghan et al. | |
| 5,908,616 A | 6/1999 | Parekh et al. | |
| 5,955,064 A | 9/1999 | Giovanniello et al. | |
| 6,066,314 A | 5/2000 | Tang et al. | |
| 6,074,632 A | 6/2000 | Shen | |

FOREIGN PATENT DOCUMENTS

EP  0653203 A1  5/1995

*Primary Examiner*—Shelley A. Dodson
(74) *Attorney, Agent, or Firm*—Arthur J. Plantamura

(57) ABSTRACT

A stable aluminum-zirconium aqueous solution of enhanced efficacy having a high concentration free of amino acid and polyhydric alcohol is disclosed. Such aluminum-zirconium salts are selected from aluminum/zirconium tetrachlorohydrate; aluminum/zirconium pentachlorohydrate, and aluminum/zirconium octachlorohydrate in which the aluminum to zirconium (Al/Zr) atomic ratio of said salt falls within the limits of the shaded areas A, B, and C, respectively, of the drawing graph wherein the aluminum/zirconium tetrachlorohydrate has an Al/Zr atomic ratio from about 2 to about 6 and metal/chloride molecular ratio about 0.9 to about 1.25; aluminum/zirconium pentachlorohydrate having Al/Zr atomic ratio from about 6 to about 10 and metal/chloride atomic ratio from about 1.5 to about 1.65; and aluminum/zirconium octachlorohydrate having Al/Zr molecular ratio from about 6 to about 10 and metal/chloride molecular ratio from about 0.9 to about 1.5.

18 Claims, 2 Drawing Sheets

STABLE ALUMINUM/ZIRCONIUM ANTIPERSPIRANT SOLUTION FREE OF AMINO ACID AND POLYHYDRIC ALCOHOL

This invention relates to improved stable aluminum-zirconium antiperspirant solutions of which avoid the inclusion of amino acids and polyhydric alcohols and possess high efficacy and to methods of preparation.

BACKGROUND OF THE INVENTION

Aluminum-zirconium compounds are well known as effective antiperspirants. The presence of zirconium species however, decreases the stability of the corresponding aluminum-zirconium antiperspirant solutions because zirconium hydrolysis species precipitate at a relative lower pH than the polymeric aluminum species. An amino acid, such as glycine, is added to stabilize the corresponding aluminum-zirconium antiperspirant solution. The coordination between zirconium and glycine stabilizes the zirconium species from gelling up in aqueous solution. Various patents are known that reference commercial aluminum-zirconium-glycine salts (ZAG) and compositions contain glycine, with the Zr:glycine weight ratio being approximately 1:1. While not wishing to be bound by a specific theory, it is believed that the addition of glycine decreases the efficacy of the corresponding aluminum-zirconium antiperspirant because of the coordination between zirconium and glycine.

U.S. Pat. Nos. 4,775,528; 5,114,705; 5,225,187; 5,486,347; 5,589,196; 5,955,064; 6,066,314; 6,074,632; EP 0 653 203 A1, for example, disclose antiperspirant compositions containing both glycine and polyhydric alcohols. As has been described in co-pending U.S. patent application Ser. No. 10/185,299 filed on Jun. 28, 2003, a stable and highly effective aluminum-zirconium antiperspirant solution is obtained by eliminating glycine and introducing polyhydric alcohol. While the introduction of polyhydric alcohol to aluminum-zirconium antiperspirant solution without glycine increases the efficacy of the antiperspirant, it also tends to introduce an undesirable tackiness to the corresponding antiperspirant active. Thus it is highly desirable to have a stable and effective aluminum-zirconium solution not only free of glycine but also free of polyhydric alcohol.

U.S. Pat. No. 2,906,668 to Beekman described aluminum-zirconium antiperspirants made by heating a zirconium salt compound with a source of aluminum hydroxychloride for a long period; or by heating a zirconium oxychloride with an aqueous solution of aluminum chloride and aluminum metal until reaction is complete. Both methods involve the employment of the heat treatment and the formation of gel during the preparation. The formation of the gel during the process of making usually results an antiperspirant composition that is less effective.

U.S. Pat. No. 2,854,382 to Grade related to an aqueous composition consisting from about 5% to about 30% by weight aluminum-zirconium salt and from 0% to 17% by weight of amino acid. It is mentioned in the patent that the amount of amino acid added is directly related to the concentration of the aluminum-zirconium salt. About 17.5% by weight of amino acid is required for a 30% by weight of aluminum-zirconium solution and about 11.5% by weight of amino acid is needed for a 20% antiperspirant salt solution. In fact, the inventors have found that when the concentration of the salts is about 10% or less by weight, no amino acid is required to prevent gelling of the solution. It is believed, however, that the zirconium species polymerize substantially in the dilute aluminum-zirconium that results in a decrease in efficacy of the corresponding antiperspirant solution. It is highly desirable to provide a stable and concentrated aluminum-zirconium antiperspirant solution that is both very effective and economical to produce.

We have now discovered that under two circumstances a stable aluminum-zirconium antiperspirant solution can be made at room temperature (RT). First, at low metals/chloride (M/Cl) atomic ratio, i.e., from about 0.9 to about 1.25, an aluminum-zirconium tetrasalt solution is prepared with excellent stability. Second, at higher Al/Zr atomic ratio, i.e. from about 6 to about 10, stable aluminum-zirconium octa and penta salt solutions are formed. Under both conditions the aluminum-zirconium antiperspirant solutions showed excellent stability.

Accordingly from the standpoint of providing a more economical while very efficacious antiperspirant and from the status of the known prior art, it is desirable to provide a stable aluminum-zirconium antiperspirant composition that possesses a high active content, that does not require the inclusion of amino acid or polyhydric alcohol.

SUMMARY OF THE INVENTION

The present invention provides a novel aluminum-zirconium (Al—Zr) composition comprising, in percent by anhydrous solid (A.S.), about 15 to about 40% antiperspirant active derived from specific aluminum zirconium salts, i.e., the salts selected from aluminum-zirconium tetrachlorohydrate, aluminum-zirconium octachlorohydrate and pentachlorohydrate and from about 60 to about 85% by weight of water. The invention provides a method of making stable aluminum-zirconium efficacious antiperspirant solutions, i.e. for making economical solutions that are effective, wherein both aluminum and zirconium function fully as antiperspirants, and in which the addition of amino acid stabilizers or polyhydric alcohols to the antiperspirant composition is not needed.

In accordance with the method of the present invention, a stable and highly efficacious aqueous antiperspirant solution is to be prepared consisting essentially of from about 15 to about 40 percent anhydrous solid of a salt selected from aluminum/zirconium tetrachlorohydrate, aluminum/zirconium octachlorohydrate, and aluminum/zirconium pentachlorohydrate, in which the aluminum/zirconium tetrachlorohydrate has an Al/Zr atomic ratio of from about 2 to about 6 and metal/chloride atomic ratio of about 0.9 to about 1.25; aluminum/zirconium octachlorohydrate having Al/Zr atomic ratio from about 6 to about 10 and metal/chloride atomic ratio from of about 0.9 to about 1.5, and aluminum/zirconium pentachlorohydrate having Al/Zr atomic ratio from about 6 to about 10 and metal/chloride atomic ratio from about 1.5 to about 1.65.

DETAILED DESCRIPTION OF THE DRAWINGS

DETAILED DESCRIPTION OF THE INVENTION

Figure 1:
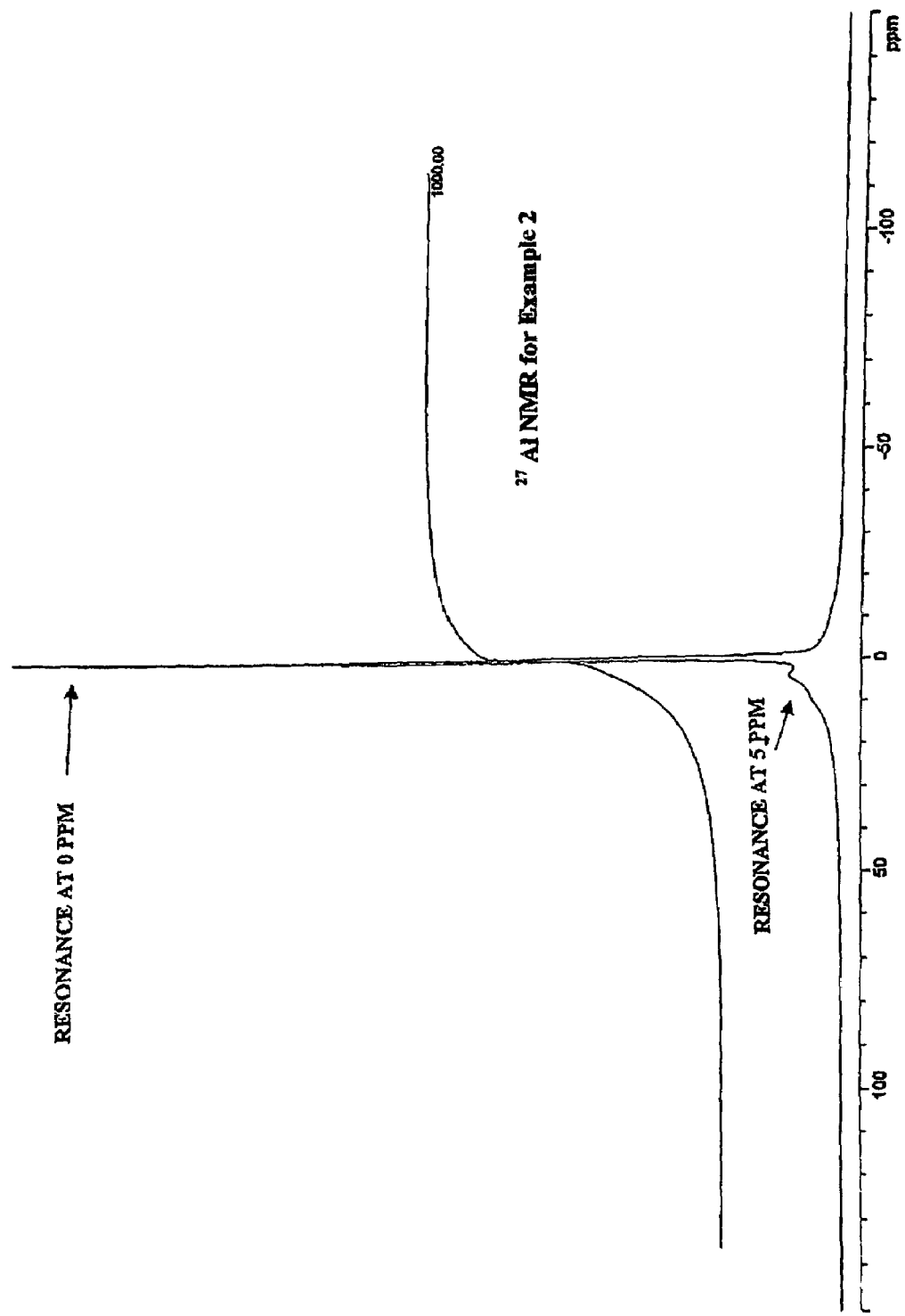
FIG. 1 is a $^{27}$Al NMR chromatogram of a solution obtained according to the present invention.

The stable aluminum-zirconium antiperspirant solution free of amino acid and polyhydric alcohols can be prepared by mixing basic aluminum halides and nitrates of the formula:

$$Al_2(OH)_{6-a}X_a$$

wherein X is Cl, Br or $NO_3$, wherein a is from about 1 to 2 so that said basic aluminum halides having an aluminum: anion ratio of 2 to 1, with a zirconium compound of the formula:

$$ZrO(OH)_b X_{2-b}$$

wherein b is a numerical number from 0 to 1.3 and X is Cl, Br or $NO_3$ at a temperature not greater than 80° C., and preferably at room temperature.

The basic aluminum halides may be made by either of two processes. First, by the method that is disclosed in U.S. Pat. No. 5,908,616 to Parekh, i.e. reacting (a) aluminum powder, (b) an aluminum halide or nitrate solution and (c) water at a temperature greater than about 85° C. Second, by mixing and reacting about 50% aluminum chlorohydrate with $AlCl_3$ or HCl at a temperature from about RT to about reflux for a period that may range from about 0.5 hr to 2 days.

The zirconium halide complexes can be prepared by mixing basic zirconium carbonate with hydrochloric acid or zirconium oxychloride at an elevated temperature. Once the clear solution is formed, it is heated at a temperature of from about 80° C. to about 100° C. for 0.5 hr to 4 hrs to eliminate the $CO_2$ that is present in the zirconium solution.

The preferred solutions contain about 25% to about 35% of anhydrous solid that are not tacky and easy to make; contain a high content of active antiperspirant species; and are stable without the requirement of adding additional relatively expensive stabilizers. The selected Al/Zr salts discovered to be suitable in accordance with the invention are, as the above mentioned, selected salts, i.e., aluminum/zirconium tetrachlorohydrate, aluminum/zirconium pentachlorohydrate, and aluminum/zirconium octachlorohydrate and which: for the aluminum/zirconium tetrachlorohydrate, has an Al/Zr atomic ratio from about 2 to about 6 and a metal/chloride atomic ratio is from about 0.9 to about 1.25; for the aluminum/zirconium pentachlorohydrate, an Al/Zr atomic ratio from about 6 to about 10 and a metal/chloride atomic ratio of from about 1.5 to about 1.65; and for the aluminum/zirconium octachlorohydrate, an Al/Zr atomic ratio from about 6 to about 10 and a metal/chloride atomic ratio of from about 0.9 to about 1.5.

The resultant aluminum-zirconium antiperspirant solutions contain high anhydrous solids active in the range of about 20 to about 40 percent, preferably from about 25 to about 35 weight percent, and most preferably from about 30 to about 35 percent of the anhydrous solid. The aluminum-zirconium antiperspirant solution can be dried by conventional methods such as spray drying and/or freeze drying.

The degree of polymerization of aluminum complexes can be determined by the high performance liquid chromatography (HPLC). The highest molecular weight Al species are eluted first, designated as Band I. Bands II and III designate intermediate molecular weight Al complexes. Band IV designates the lowest molecular weight Al complexes, including monomers and dimmers. The relative area of one or more peaks is determined in order to characterize the distribution of polymeric species in the aluminum complexes formed. It has been observed by the invention that an aluminum-zirconium tetrasalt solution with low M/Cl ratio generally has high % Band IV HPLC profile that decreases with the increase of the M/Cl ratio. The trend is similar to what had been observed with aluminum-zirconium-glycine antiperspirant solution.

A Phenominex Column and a Waters Column connected in series are used to obtain a HPLC Chromatograph. A sample of 2% by weight of aluminum is filtered through a 45-micron filter and chromatographed within 10 minutes using a 0.01N nitric acid solution as the mobile phase.

The stability of the novel aluminum-zirconium solution is measured by Brookfield viscometer. The stable solution is characterized by the quality in which no significant change in viscosity is observed in the solution upon aging at RT.

$^{27}$Al nuclear magnetic resonance (NMR) is employed to determine the structure of aluminum in aluminum-zirconium salt solution. $^{27}$Al NMR spectra of the solutions were collected using a Tecmag Libra System SDS 360-1. The data were collected from about +150 to −150 ppm. The $^{27}$Al NMR of the aluminum-zirconium tetrasalt solutions indicate the formation of large amounts of low molecular weight aluminum species. The amount of low molecular weight aluminum species decreases with the increase of M/Cl atomic ratio.

It is seen that in essence, the present invention provides a method of making stable antiperspirant solutions of aluminum and zirconium having high efficacy, i.e., having a high proportion of lower molecular weight aluminum species, while excluding polyhydric alcohols and amino acids stabilizers.

The invention will be further illustrated by the following Examples. In the Examples, parts are by weight unless otherwise specified. Anhydrous solid content is given as % A.S.

EXAMPLE 1

Figure 2:
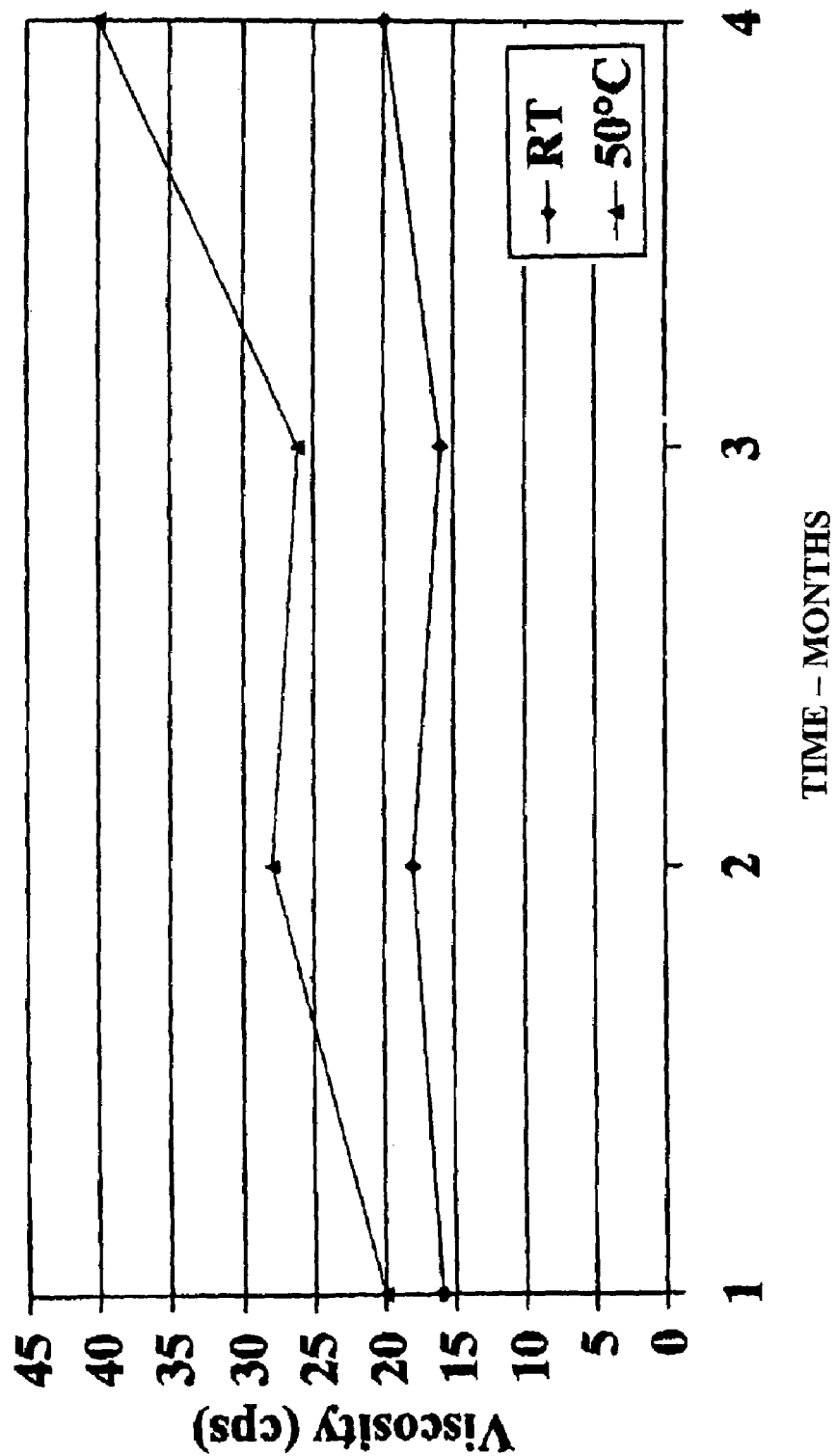
FIG. 2 is a viscosity stability profile over time at RT and at 50° C. of the antiperspirant solution of the invention.

1528 parts of Basic Aluminum Chloride (BAC, 10.73% Al, 11.89% Cl) was mixed with 244 parts of $ZrOCl_2$, followed by the addition of 228 parts of water. The mixture was mixed at RT for one hour, which was filtered to give a clear colorless solution. Chemical analysis is as follows: 8.22% Al; 3.22% Zr; 12.0% Cl; M/Cl ratio of 1.0 and 35.6% A.S. The solution has an initial viscosity of 14.0 cps, which increased to 26.0 cps after one year at RT. A viscosity profile over time is illustrated by FIG. 2 of the drawing.

Examples 2, 3, 4, 5 and 6 were carried out similar to Example 1 except in some cases zirconium hydroxy chloride (ZHC) was used, which was generally heated at 90° C. for 2 hrs before mixing with BAC. The results are listed in Table 1.

TABLE 1

| Example | Al/Zr ratio | M/Cl ratio | % A.S. | viscosity (cps) | % Band IV |
|---------|-------------|------------|--------|-----------------|-----------|
| 2 | 3.6 | 0.96 | 33.0 | 22.0 | 53.7 |
| 3 | 3.6 | 1.25 | 33.7 | 8.0 | 36.8 |
| 4 | 6.5 | 1.06 | 33.0 | 8.0 | 47.8 |
| 5 | 6.5 | 1.56 | 31.2 | 10.0 | 15.8 |
| 6 | 8.2 | 1.58 | 31.6 | 4.0 | 22.0 |

Although the present invention has been described in terms of specific embodiments, the invention is not meant to be so limited. Various changes can be made to the composition and proportions used while still obtaining the benefits of the invention. Thus the invention is only to be limited by the scope of the appended claims.

What is claimed:

1. A stable and highly efficacious aqueous antiperspirant solution free of amino acid and polyhydric alcohol and consisting essentially of from about 15 to about 40 percent anhydrous solid of a salt selected from aluminum/zirconium tetrachlorohydrate, aluminum/zirconium pentachlorohydrate, and aluminum/zirconium octachlorohydrate in which the aluminum to zirconium (Al/Zr) atomic ratio of said salt falls within the limits of the shaded areas A, B, and C, of the drawing graph and wherein, respectively, the aluminum/zirconium tetrachlorohydrate has an Al/Zr atomic ratio from about 2 to about 6 and metal/chloride atomic ratio about 0.9 to about 1.25; aluminum/zirconium pentachlorohydrate having Al/Zr atomic ratio from about 6 to about 10 and metal/chloride atomic ratio from about 1.5 to about 1.65; and aluminum/zirconium octachlorohydrate having Al/Zr atomic ratio from about 6 to about 10 and metal/chloride atomic ratio from about 0.9 to about 1.5.

2. The antiperspirant solution of claim 1 wherein the salt is the aluminum/zirconium octachlorohydrate.

3. The antiperspirant salt of claim 1 wherein the salt is the aluminum/zirconium tetrachlorohydrate.

4. The antiperspirant salt of claim 1 wherein the salt is the aluminum/zirconium pentachlorohydrate.

5. The antiperspirant salt of claim 2 wherein the percent of the anhydrous salt is from about 20 to about 40.

6. The antiperspirant salt of claim 3 wherein the percent of the anhydrous salt is from about 20 to about 40.

7. The antiperspirant salt of claim 4 wherein the percent of the anhydrous salt is from about 20 to about 40.

8. The antiperspirant solution according to claim 1 which is dried to a powder.

9. A method of making stable aluminum-zirconium salt solution free of amino acid and polyhydric alcohol which comprises mixing and reacting basic aluminum halides and nitrates of the formula:

wherein X is Cl, Br and/or $NO_3$, wherein a is from about 1 to 2 with a zirconium compound of the formula:

wherein b is a numerical number from 0 to 1.3 and X is Cl, Br and/or $NO_3$ at temperature not in excess of about 80° C.

10. The method of claim 9 wherein the reaction is at room temperature.

11. The method of claim 9 wherein the basic aluminum halides and nitrate employed in the reaction is made by reacting (a) aluminum powder, (b) an aluminum halide or nitrate solution and (c) water at a temperature greater than about 85° C.

12. The method of claim 9 wherein the basic aluminum halides and nitrate is made by mixing about 50% aluminum chlorohydrate with $AlCl_3$ or HCl from about room temperature to about reflux for a period of about 0.5 hr. to 2 days.

13. The method of claim 9; wherein the zirconium halide complex is made by mixing basic zirconium carbonate with HCl or zirconium oxychloride at a temperature of about 50–70° C. until the solution is clear.

14. The method of claim 13 wherein the zirconium halide complex is heated at about 80–100° C. for 0.5 to 4 hrs.

15. The method of claim 9 wherein the aluminum-zirconium solution is dried to a powder.

16. A roll on formulation in which the solution of claim 1 is the active ingredient.

17. A clear gel formulation in which the solution of claim 1 is the active ingredient.

18. An antiperspirant stick formulation in which the powder of claim 8 is the active ingredient.

* * * * *